United States Patent [19]

Braithwaite

[11] 4,285,242
[45] Aug. 25, 1981

[54] PIPE INSPECTION APPARATUS

[75] Inventor: Geoffrey C. Braithwaite, Wantage, England

[73] Assignee: British Gas Corporation, London, England

[21] Appl. No.: 67,790

[22] Filed: Aug. 20, 1979

[30] Foreign Application Priority Data

Feb. 28, 1979 [GB] United Kingdom ............... 07149/79

[51] Int. Cl.³ ............................................ G01N 29/04
[52] U.S. Cl. ........................................ 73/623; 73/639; 324/220
[58] Field of Search ................. 73/623, 638, 639, 637, 73/633; 324/220; 250/358 P

[56] References Cited

U.S. PATENT DOCUMENTS

| 3,238,448 | 3/1966 | Wood et al. | 324/220 |
|---|---|---|---|
| 3,413,653 | 11/1968 | Wood | 73/40.5 A |
| 3,478,576 | 11/1969 | Bogle | 73/40.5 A |
| 3,754,275 | 8/1973 | Carter et al. | 73/40.5 R |
| 3,786,684 | 1/1974 | Wiers et al. | 73/432 R |
| 4,055,990 | 11/1977 | Topping | 73/623 |
| 4,105,972 | 8/1978 | Smith | 73/638 X |
| 4,117,402 | 9/1978 | Zangger et al. | 324/220 |
| 4,170,902 | 10/1979 | Pallan | 73/432 R |
| 4,217,782 | 8/1980 | Pont | 73/638 X |

FOREIGN PATENT DOCUMENTS

| 369485 | 8/1973 | U.S.S.R. | 73/623 |
|---|---|---|---|
| 550573 | 8/1977 | U.S.S.R. | 73/623 |

Primary Examiner—Daniel M. Yasich
Attorney, Agent, or Firm—Watson, Cole, Grindle & Watson

[57] ABSTRACT

A pipe inspection apparatus includes a vehicle which is capable of moving along the bore of the pipe, two rubber cup-shaped members at each end of the vehicle for aligning the vehicle lengthwise in the pipe, a floating assembly of inspection devices such as ultrasonic transducers disposed circumferentially around the vehicle, and at least four link members pivotally attached to the assembly and to the vehicle to constrain the assembly to move in a direction normal to the length of the vehicle. The assembly may be resiliently suspended from the vehicle, and may also be provided with a centralizing device, such as a rubber cup-shaped member or rollers or skids, to centralize the assembly in the bore of the pipe.

12 Claims, 3 Drawing Figures

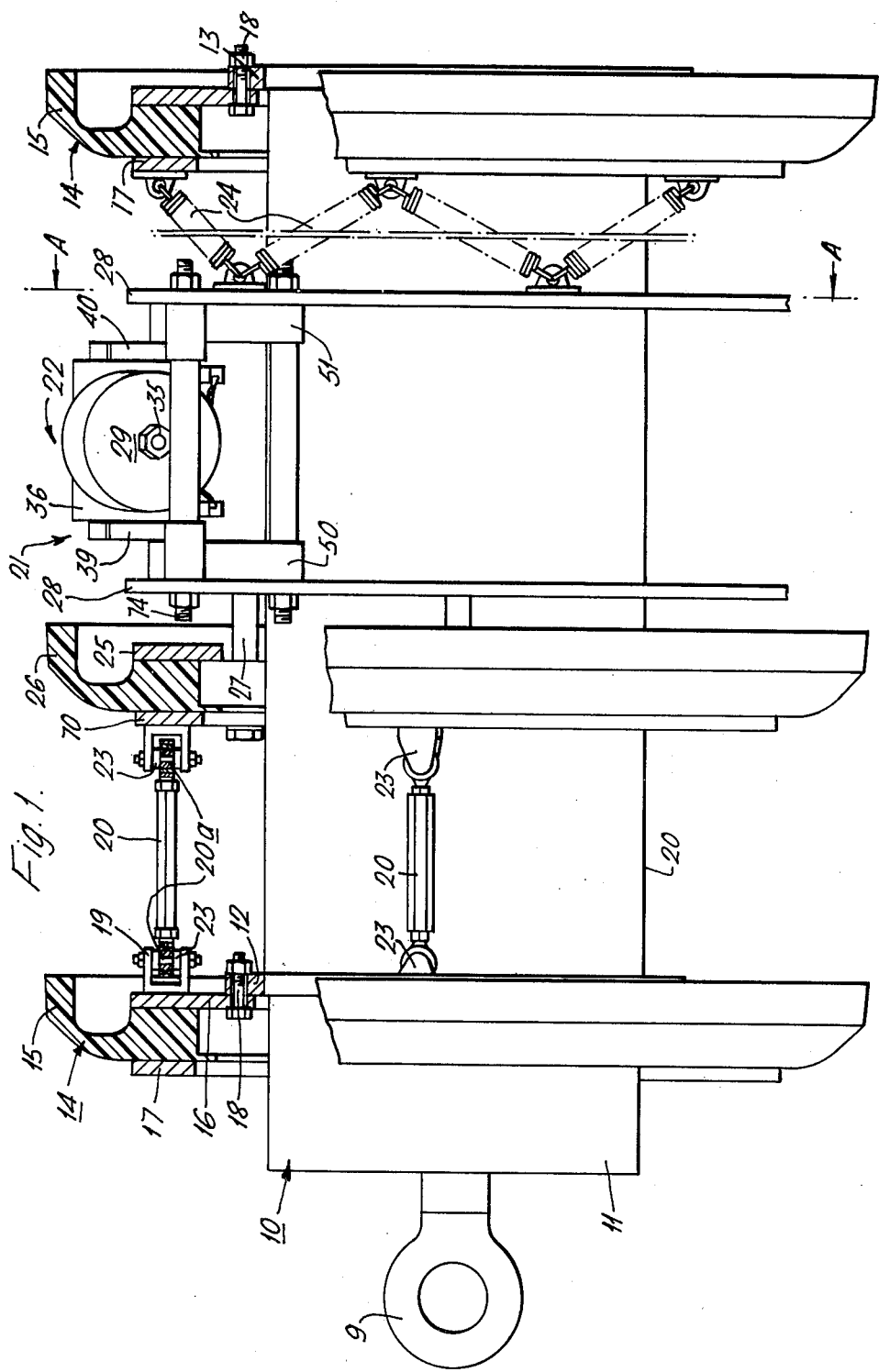

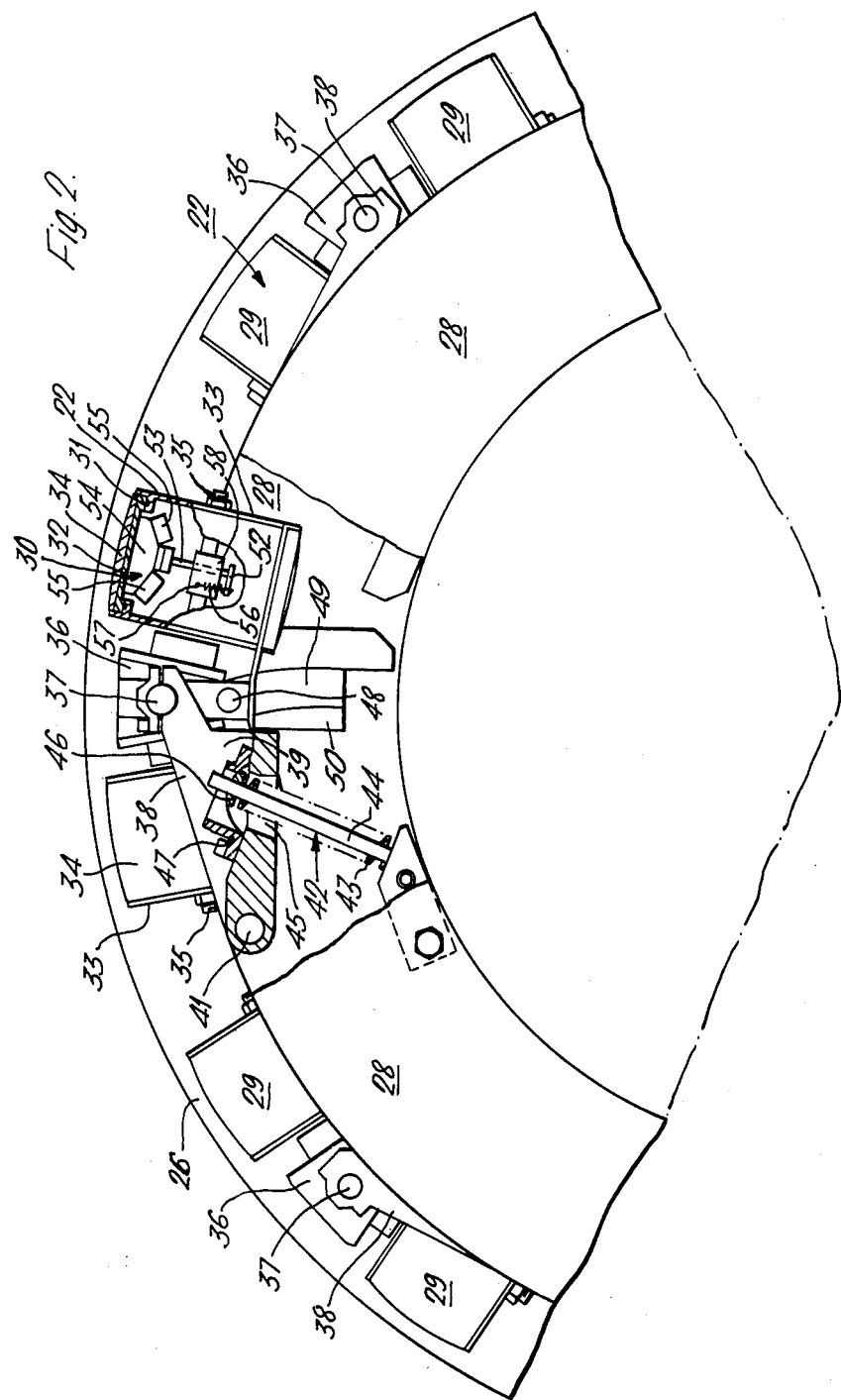

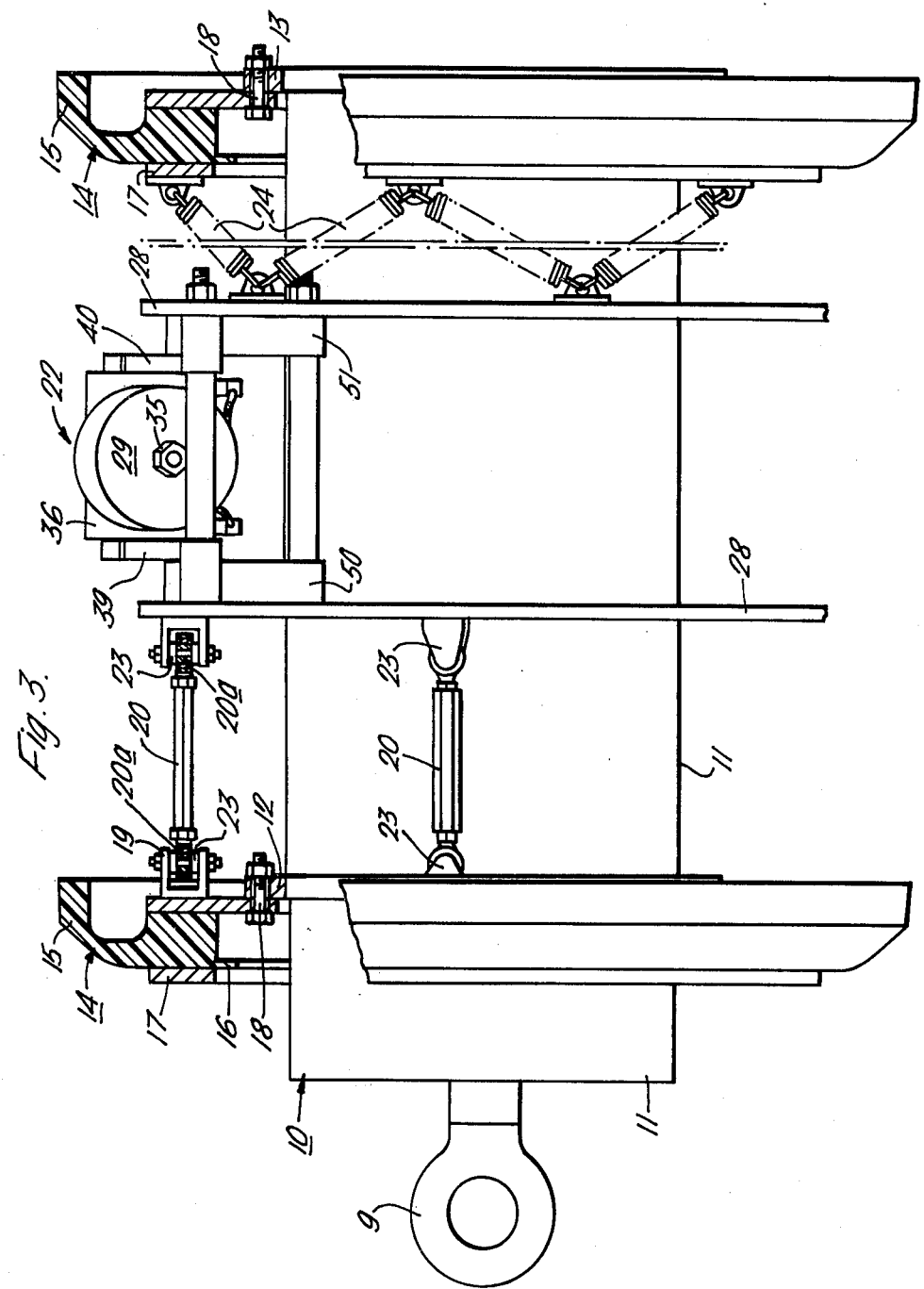

PIPE INSPECTION APPARATUS

BACKGROUND OF THE INVENTION

1. Field of the Invention

This invention relates to pipe inspection apparatus of the type which is inserted into the bore of a pipe for the purpose of examining the wall of the pipe for defects, cracks or other discontinuities.

2. The Prior Art

The usual pipe inspection apparatus for examining, for example, gas pipelines comprises a vehicle, or a train of vehicles, which is propelled along the pipeline by the gas flow in the pipeline.

One favored technique for examining the walls of the pipe as the vehicle is propelled along the pipe uses ultrasonic probes. In one arrangement, ultrasonic transducers are mounted in a number of wheels which are urged into contact with the wall of the pipe. In use, ultrasound generated by the transducers is transmitted across the interface between the wheel and the wall of the pipe into the pipe wall. Ultrasound reflected or refracted from within the pipe wall is in turn received by the transducers within the wheels and subsequently analyzed. This technique requires intimate contact at all times between the wheel and the pipe wall so as to reduce or eliminate losses of the ultrasound signal at the interface between the wheel and the pipe wall.

Another important consideration is that the ultrasonic transducers, and hence the wheels, must be correctly aligned in the pipe. In one arrangement, a plurality of wheel probes are equispaced around the inner circumference of the pipe and arranged so that the wheels roll along the length of the pipe. The transducers inside the wheels are arranged to examine the pipe wall over a band which lies in a plane normal to the longitudinal axis of the pipeline. It is relatively easy to achieve a band normal to the longitudinal axis of the pipe on straight runs of the pipeline if the assembly of wheel probes are located midway along an elongated vehicle which is provided at each end with a means for locating the vehicle concentrically in the pipe. However, it becomes more difficult to ensure that the transducers are correctly aligned in the pipe and are also urged against the wall of the pipe with sufficient pressure to ensure intimate contact when the vehicle is negotiating a bend. This is because those wheel probes on the inside of the bend will tend to be forced against the pipe, whereas those on the outside of the bend will tend to be pulled away from the pipe wall.

An object of the present invention is to provide pipe inspection apparatus which will cater to bends in the pipe-line, and, in some cases, will accommodate changes in the diameter of the pipeline, without upsetting, to an unacceptable degree, the alignment, positioning and degree of contact of the wheel probes in the bore of the pipeline.

SUMMARY OF THE INVENTION

According to one aspect of the present invention there is provided a pipe inspection apparatus comprising a vehicle capable of movement along the bore of a pipe, alignment means on the vehicle for aligning the vehicle lengthways along the bore of the pipe, an assembly of inspection devices arranged for examining a circumferential band of the wall of the pipe, the assembly being movable bodily relative to the vehicle, and constraining means for constraining the assembly to move in a direction normal to the length of the vehicle to allow the assembly to align itself relative to the pipe but such that the circumferential band lies substantially normal to the bore of the pipe.

The assembly may be suspended from the vehicle on resilient members such as springs. The alignment means may comprise one or more devices for contacting the bore of the pipe at three or more points around the circumference of the pipe at each end of the vehicle. Preferably, the alignment means comprises a flexible annular or circular member which contacts the bore of the pipe around at least a major part of its circumference. The flexible, annular or circular member may be shaped so that the pressure of the fluid when used in the bore of a pipe containing pressurized fluid urges the member into sealing engagement with the bore of the pipe.

Preferably, the inspection devices include ultrasonic transducer means for transmitting sound into the wall of the pipe and for receiving sound from within the wall of the pipe.

Preferably, the transducer means are mounted within wheels arranged to roll along the length of the pipe as the vehicle moves along the pipe. Preferably, the wheel probes are biased radially outwardly so as to engage the pipe.

The wheel probes may be constructed in accordance with U.S. Pat. No. 4,202,216 or in accordance with U.S. patent application Ser. No. 933,031, filed Aug. 11, 1978, now abandoned, and U.S. Pat. No. 4,202,216.

The inspection devices may comprise magnetic devices for magnetizing the pipe wall and monitoring devices for monitoring flux leakages or perturbations in the magnetic pattern. It may be possible to use other types of inspection devices, such as for example, eddy current testing devices.

DESCRIPTION OF THE DRAWINGS

An embodiment of the invention will now be described by way of an example with reference to the accompanying drawings in which FIG. 1 is a part sectional side elevation of apparatus constructed according to the present invention for ultrasonically inspecting the wall of a pipe;

FIG. 2 is a fragmentary, partly broken away, end view, looking in the direction of arrow A of FIG. 1; and FIG. 3 is a fragmentary part sectional side elevation of an alternative apparatus to that of FIG. 1.

DETAILED DESCRIPTION OF THE PREFERRED EMBODIMENT

Referring to FIG. 1, the apparatus is intended for insertion in a 24-inch diameter gas pipeline (not shown) and comprises a vehicle 10 provided with a towing eye 9 which enables the vehicle 10 to be towed by a second vehicle (not shown) which is propelled along the pipeline by the flow of pressurized gas in the pipe.

The vehicle 10 comprises a central hollow tubular member 11 having two flanges 12 and 13, each of which is located at or near respective ends of the vehicle. Alignment means 14 are mounted on each flange for the purpose of locating and aligning the vehicle 10 along the axis of the pipe. Each alignment means 14 comprises an annular sealing member 15 made of an elastomeric material such as polyurethane and has a concave recess facing towards the rear of the vehicle 10 so that pressurized gas in the pipe urges the annular sealing member 15 into engagement with the bore of the pipe. Each annular sealing member 15 is clamped between an annular plate 16 and a clamping plate 17, and the annular plates 16 are secured by bolts 18 to the respective flanges 12, 13.

Four brackets 19 equispaced around a common pitch circle are secured to the front annular plate 16, and a link 20 is mounted by a spherical ball joint 20a at one end to a pivot 23 in each bracket 19 to provide the constraining means. A spherical ball joint 20a in the free end of each of the links 20 locates about a pivot 23 in a respective bracket 19 secured to an annular support plate 70, the brackets 19 being arranged so that the pivots 23 lie approximately radially relative to the front annular plate 16.

The support plate 70 forms part of a carrier 21 having two annular carrier plates 28 spaced apart in parallel relationship by hollow spacers 71 and secured together by bolts 74 extending through the spacers 71, the bolted-together carrier plates 28 being fixed to the support plate 70 by bolts 27. The carrier 21 is freely movable in a plane normal to the longitudinal axis of the vehicle 10, and is suspended on springs 24 attached to the annular plate 17 of the rearmost alignment means 14 and the rearmost carrier plate 28. The carrier 21 has a rubber centralizing member 26 clamped between a clamping plate 25 and the support plate 70 to centralize the carrier 21 in the bore of the pipe. Eight inspection devices 22 are resiliently supported between the carrier plates 28 as shown in greater detail in FIG. 2 to which reference is also made.

Each inspection device 22 comprises two hollow wheels 29, each wheel 29 having inside thereof an ultrasonic probe assembly 30 with transducers 55 arranged to transmit sound into the wall of the pipe so that the sound travels around a circumferential band of the pipe wall. Power for energizing the transducers 55, together with the signals representative of the sound received from within the pipe, are fed by way of leads (not shown) either to the towing vehicle or to a further vehicle (not shown) which is towed behind the vehicle 10. Each wheel 29 comprises an hermetically sealed hollow body 31 made of polymethylmethacrylate (Perspex—a Registered Trade Mark), rim 32 and brass sideplates 33 secured to the rim 32. The rim 32 is provided with a solid polyurethane tire 34 around its circumference. The wheels 29 are mounted for rotation on a spindle 35 carried by a tapered block 36. The block 36 is itself pivotally mounted on a spindle 37 carried at the free end of the limbs of a generally "U" shaped pivot arm 38. The wheels 29 are thereby able to pivot about the axis of the spindle 37 so that the two wheels of each inspection device 22 contact the bore of the pipe along lines which are equispaced on each side of a radial plane passing through the longitudinal axis of the pipe and the longitudinal axis of spindle 37.

The ultrasonic probe assembly is resiliently carried by the spindle 35 and the hollow wheel contains an acoustic coupling medium (not shown) such as, for example, a mixture of glycerol and water. In some cases this mixture may be loaded with particles of carbon, for example, graphite, or molybdenum disulphide. The size of the particles is chosen so as to attenuate slightly the ultrasound, thereby reducing ultrasonic reverberation within the wheel after transmission of an ultrasonic pulse from a transducer.

The ultrasonic probe assembly 30 includes a support structure, consisting of brackets 52 and rods 53, which are arranged to support a nylon block 54 upon which are mounted a plurality of transducers 55, for transmitting ultrasound into the wall of the pipe and for receiving sound scattered or reflected from the wall of the pipe. The block 54 is urged against the inside surface of the rim 32 by a tension spring 56 which is anchored between one of the brackets 52 and a pin 57 secured in a central block 58 which forms part of the spindle 35. The rods 53 are slidably supported in the spindle block 58 for linear movement of the probe assembly. The block 54 is shaped to conform with the shape of the inside surface of the rim 32, so as to ensure that the beams of sound from the transducers 55 enter the pipe wall at a predetermined preferred angle, and that the acoustic coupling medium is permitted to penetrate any gaps between the transducers 55 and the block 54 and between the block 54 and the rim 32. Electrical leads (not shown) from the transducers 55 pass along a bore (not shown) in the spindle 35 through seals which prevent the acoustic coupling medium leaking from the wheel 29 and out through the tapered block 36.

The pivot arm 38 comprises two spaced apart side members 39, 40 connected by a shaft 41 about which the pivot arm 38 rotates. The pivot arm 38 is mounted between the carrier plates 28, and a spring assembly 42 operates on each side member 39, 40 to urge the wheels 29 radially outwardly into engagement with the bore of the pipe. Each spring assembly 42 comprises a compression coil spring 43 mounted on a rod 44 which is rigidly mounted at one end on the rearmost carrier plate 28. The coil spring 43 passes through an elongate slot 45 in the pivot arm 38, and urges a thrust pad 46 into engagement with a concave surface of a bracket 47 secured to the pivot arm 38.

Each tapered block 36 is provided with spigots 48 which engage in guideways 49 provided in end stops 50, 51 carried by the carrier plates 28. The guideways 49 are shaped to provide a limit to the pivotal movement of tapered block 36 while allowing some pivotal movement of tapered block 36 when wheels 29 are negotiating irregularities in the pipe surfaces such as ovality or welds. This assists in maintaining the wheels 29 correctly aligned relative to the pipe wall so that the wheels 29 contact the pipe wall along lines equispaced about radial planes. Stops (not shown in detail) are provided to limit the pivotal movement of the pivot arm 38 about the shaft 41.

The use of the centralizing member 26 may be dispensed with in some applications, and reliance placed upon the coil springs 43 on the pivot arm 38 exerting a centralizing action for the carrier 21 through the thereby resiliently biased wheels 29. In such applications, the brackets 19 at the free ends of the links 20 may be mounted directly onto the forward carrier plate 28 as shown in FIG. 3 to which reference can be made, the support plate 70, clamping plate 25, and bolts 27 also being dispensed with. Alternative, centralising members may be used, such as rollers or skids.

The springs 24 although desirable may also be omitted. The wheels 29 have been described as pivotable about a pivotal pivot arm 38, but the wheels 29 could, if desired, be pivotally connected to a member (not shown) constrained to move linearly, for example, in a radially directed groove.

It will be understood that although the invention has been described in relation to the use of ultrasonic transducers as the inspection devices, other inspection devices such as magnetic inspection devices may be attached to the carrier 21.

I claim:

1. A pipe inspection apparatus which is capable of moving along the bore of a pipe, said apparatus including an elongated vehicle having a forward end and a rearward end;

a first annular alignment means attached to the side of said vehicle near its forward end to help position said vehicle within the pipe to be inspected;

a second annular alignment means attached to the side of said vehicle near its rearward end to help position said vehicle within the pipe to be inspected;

a movable assembly means positioned around said vehicle between said first and second annular alignment means, said movable assembly means including first and second spaced apart annular carrier plates, said first annular carrier plate being located nearer said first annular alignment means than said second annular carrier plate, a plurality of circumferentially spaced apart inspection means mounted between said first and second annular carrier plates near their peripheries which are capable of examining a circumferential band of the pipe wall, an annular centralizing member positioned between said first annular alignment means and said first annular carrier plate, and a number of connection means fixedly connecting said annular centralizing member with said first annular carrier plate; and a plurality of circumferentially spaced apart link means connecting said first annular alignment means with said annular centralizing member to function to constrain the movement of said assembly means in a direction towards and away from said vehicle.

2. A pipe inspection apparatus as defined in claim 1, wherein said first and second annular alignment means include elastomeric elements which each include concave annular recesses facing the rearward end of said vehicle.

3. A pipe inspection apparatus as defined in claim 1, wherein each said link means includes a first bracket means attached to the first annular alignment means on the side thereof facing said annular centralizing member, a second bracket means attached of the annular centralizing member on the side thereof facing said first annular alignment means, and a link arm connected between said first and second bracket means.

4. The pipe inspection apparatus as defined in claim 3, wherein each of said first and second bracket means includes a pivot means, wherein the ends of each link arm include spherical ball joints and wherein each spherical ball joint is positioned to pivot about a pivot means of a respective bracket means.

5. The pipe inspection apparatus as defined in claim 3, wherein four link means are utilized, each link means being equally spaced from an adjacent link means circumferentially around said vehicle.

6. The pipe inspection apparatus as defined in claim 3, wherein said vehicle comprises a hollow tubular member.

7. The pipe inspection apparatus as defined in claim 1, wherein said second annular carrier plate is connected to said second annular alignment means by a multiplicity of springs.

8. The pipe inspection apparatus as defined in claim 1, wherein said annular centralizing member is composed of rubber, and it includes a concave annular recess facing the rearward end of said vehicle.

9. The pipe inspection apparatus as defined in claim 1, wherein each said inspection means includes two hollow rotatable wheels capable of contacting the pipe wall at two circumferentially spaced apart locations, each hollow wheel including a detection device for analyzing the characteristics of the pipe wall in contact with the respective wheel.

10. The pipe inspection apparatus as defined in claim 9, wherein each detection device comprises an ultrasonic transducer.

11. The pipe inspection apparatus as defined in claim 9, wherein each inspection means further includes a tapered block mounted between said two hollow rotatable wheels, said tapered block including spindles extending from opposite sides thereof around which said hollow wheels rotate, and means to mount said tapered block.

12. The pipe inspection apparatus as defined in claim 11, wherein said means to mount said tapered block includes U-shaped pivot arm which is rotatable about a shaft such that said tapered block can move towards and away from said vehicle.

* * * * *